US00PP30629P2

(12) United States Plant Patent
Fewel

(10) Patent No.: US PP30,629 P2
(45) Date of Patent: Jul. 2, 2019

(54) CHERRY TREE NAMED 'TF 7142'

(50) Latin Name: *Prunus avium*
Varietal Denomination: TF 7142

(71) Applicant: Terry T. Fewel, Zillah, WA (US)

(72) Inventor: Terry T. Fewel, Zillah, WA (US)

( * ) Notice: Subject to any disclaimer, the term of this patent is extended or adjusted under 35 U.S.C. 154(b) by 0 days.

(21) Appl. No.: 15/998,070

(22) Filed: Jun. 21, 2018

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Annette H Para
(74) *Attorney, Agent, or Firm* — Svendsen Legal, LLC

(57) ABSTRACT

A new and distinct sweet cherry tree (*Prunus avium*) named 'TF 7142' is disclosed. 'TF 7142' is characterized by early maturing, and round-oblong shaped fruit that is dark in color.

7 Drawing Sheets

Genus and species: *Prunus avium.*
Variety denomination: 'TF 7142'.

STATEMENT REGARDING FEDERALLY SPONSORED RESEARCH OR DEVELOPMENT

None

BACKGROUND AND ORIGIN OF THE NEW VARIETY

The new cherry cultivar that has been given the variety denomination 'TF 7142', was discovered by the inventor in March of 2001, in a cultivated orchard at Zillah, Wash. 'TF 7142' has been shown to remain true to type over successive generations. Specifically, the mother tree of the naturally occurring sport 'TF 7142' is of unknown parentage, but assumed to be the 'Bing' cultivar. 'TF 7142' was discovered in an established orchard block of 'Bing' (not patented) and 'Rainer' (not patented) cherry trees, which was purchased in 1984, and is located at 3271 Roza Drive, Zillah, Wash. 98953, in Yakima County. Over the years after purchasing the orchard, occasional trees were replaced from nursery stock. In 2014, the tree 'TF 7142' that was planted in 2004 (on 'Mazzard' varietal rootstock), was noticed by the inventor to not be like the 'Bing' cultivar it was supposed to be. In 2016 and 2017, second generation scion wood of the apparent sport 'TF 7142' were grafted on 'Gisela 6' (commonly referred to as 'G6') and 'Gisela 12' (commonly referred to as 'G12') varietal rootstocks, and the subsequent fruit is identical to that of the 'TF 7142' mother tree.

The 'TF 7142' tree produces a dark sweet cherry that are unique in that the 'TF 7142' blooms approximately one week earlier than the 'Bing' cultivar, and approximately four days earlier than the 'Chelan' cultivar. The 'TF 7142' fruit mature ahead of 'Bing' and 'Chelan' and the 'TF 7142' fruit exhibit a round-oblong shape that is different than that of 'Chelan' and 'Bing'.

Throughout several generations of asexual propagation, 'TF 7142' has been observed to retain its distinctive characteristics and remain true to type.

SUMMARY OF THE NEW VARIETY

The present invention relates to a new a distinct variety of cherry tree *Prunus avium*, which has been given the variety denomination 'TF 7142'. 'TF 7142' is a dark cherry that is unique in that it blooms approximately one week earlier than the 'Bing' cultivar, and approximately four days earlier than the 'Chelan' cultivar. The 'TF 7142' fruit exhibits a round-oblong shape that is different than that of 'Chelan' and 'Bing', and matures ahead of 'Bing' and 'Chelan'. Notably, the S-allele genotype of 'TF 7142' is $S^1S^4$, whereas 'Chelan' is $S^3S^9$, and 'Bing' is $S^3S^4$. 'TF 7142' is a softer cherry than 'Chelan' and has less acid than 'Chelan'.

COMPARISON OF 'TF 7142' TO COMARISON CULTIVAR

Table 1., below, sets forth some of the distinguishing characteristics of 'TF 7142' as compared the 'Chelan' cultivar, as a closely comparable cultivar. Firmness ratings were measured using a 'Firm Tech 2' brand of firmness tester, and ratings are in milligrams needed to depress 1 millimeter. Acid is a percentage measurement of tartaric acid, and peak size is a standard fruit per row, meaning the number of cherries of a uniform size necessary to pack row-faced across a container having a 10½ inch inside width.

TABLE 1

| Cherry | Harvest Date | Ave. Firmness | pH | ° Brix | Acid | Peak Size |
|---|---|---|---|---|---|---|
| 'TF 7142' | Jun. 4, 2018 | 341 | 3.72 | 16.2 | 7.33% | 9 |
| 'Chelan' | Jun. 8, 2018 | 371 | 3.5 | 16.3 | 9.65% | 11 |

BRIEF DESCRIPTION OF THE PHOTOGRAPHS

Figure 1:
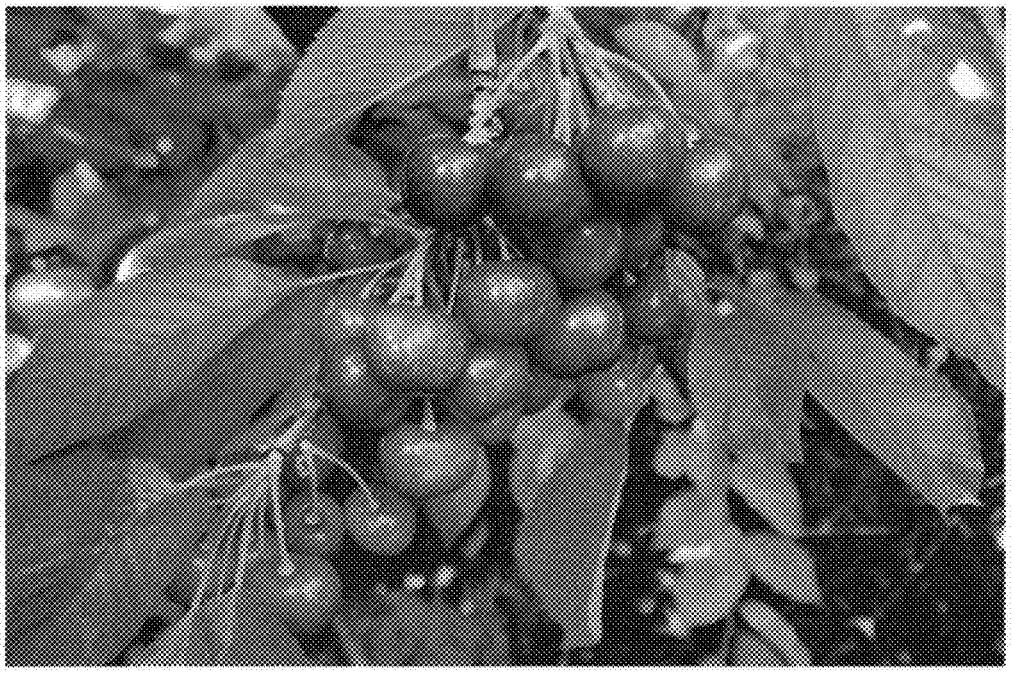
FIG. 1 is a color photograph that illustrates near mature fruit clusters of 'TF 7142'.
Figure 2:
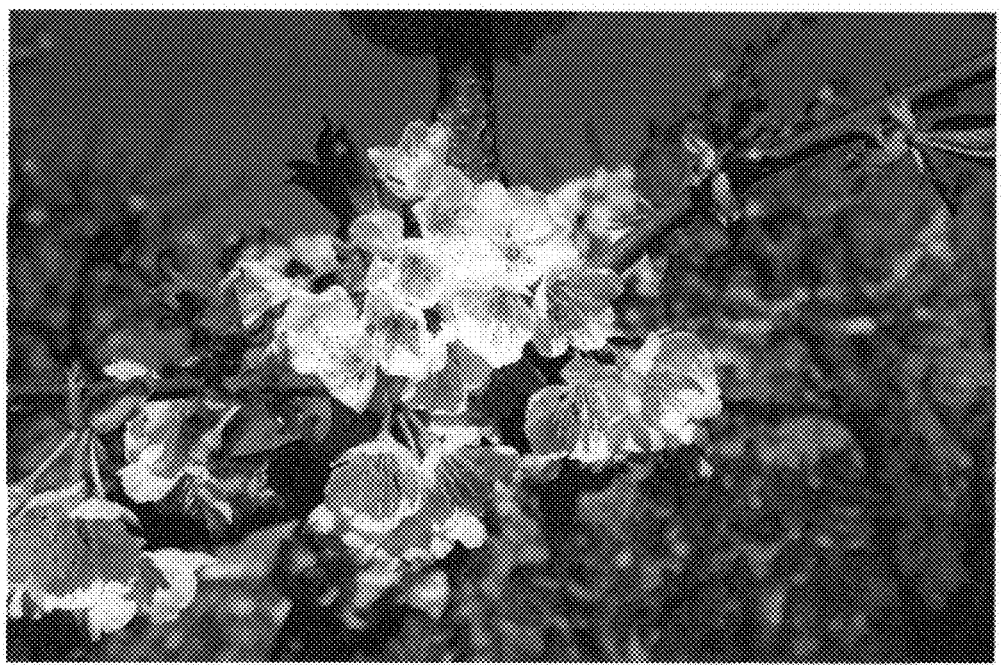
FIG. 2 is a color photograph that illustrates full bloom of blossom cluster of the 'TF 7142'.
Figure 3:
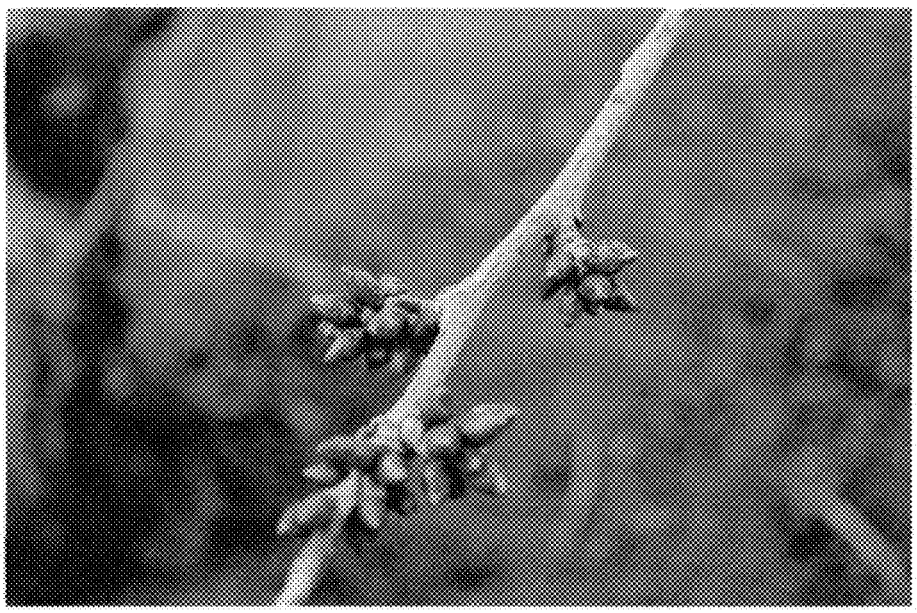
FIG. 3 is a color photograph that illustrates dormant fruiting spurs of the 'TF 7142'.
Figure 4:
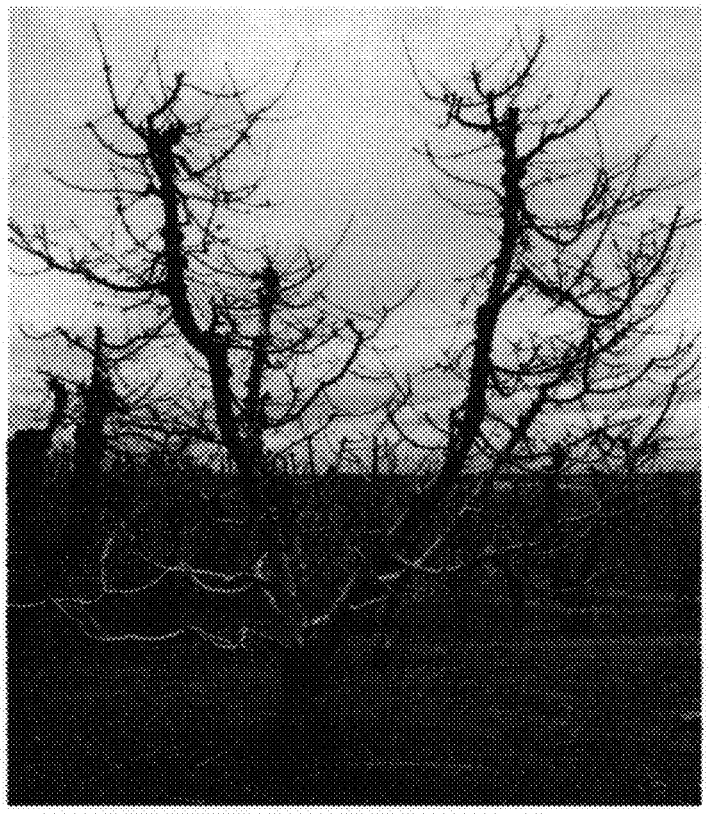
FIG. 4 is a color photograph that illustrates the 'TF 7142' mother tree at full dormancy.
Figure 5:
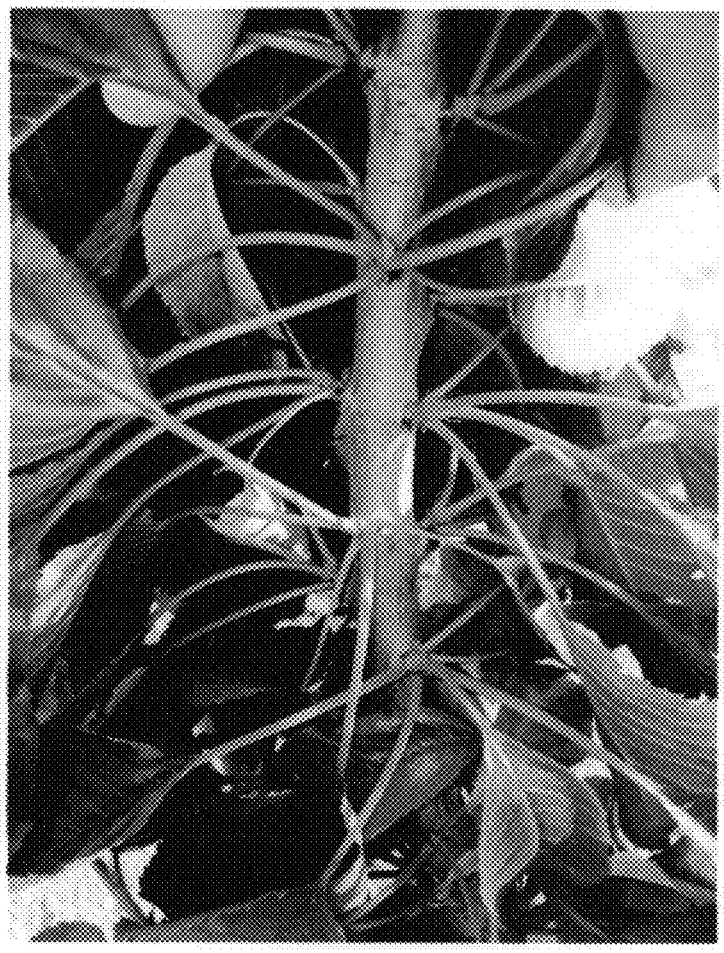
FIG. 5 is a color photograph that illustrates the foliage of the 'TF 7142'.
Figure 6:
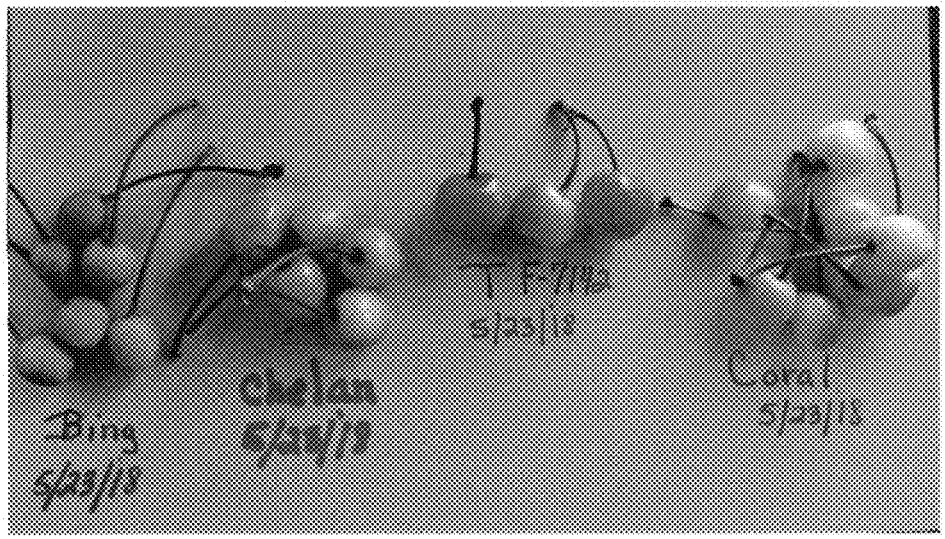
FIG. 6 is a color photograph that illustrates a comparison between the fruits of 'Bing', 'Chelan', 'Coral', and 'TF 7142' cherry varieties, as present in the same orchard on May 23, 2018.
Figure 7:
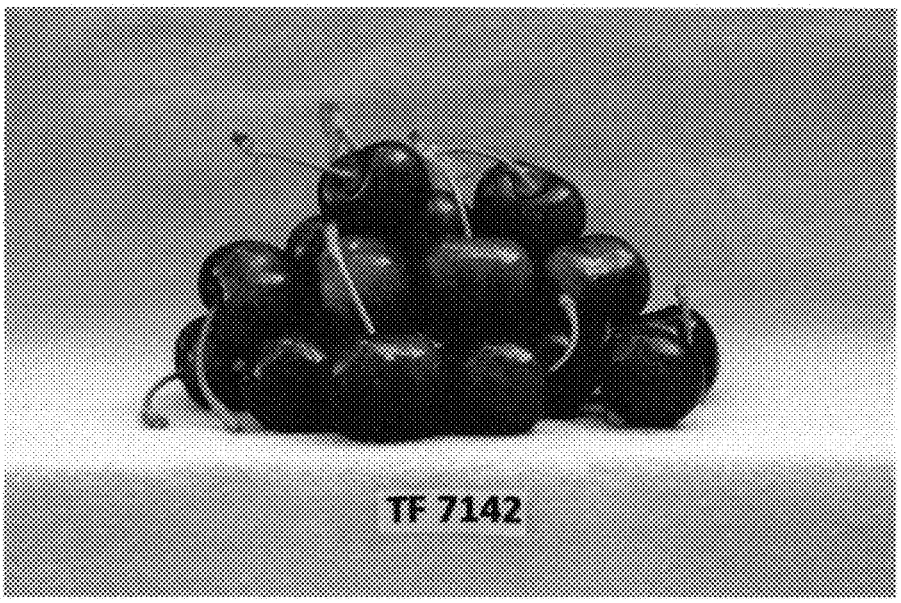
FIG. 7 is a color photograph that illustrates of 'TF 7142' cherries at harvest maturity.

The colors of these photographic illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2016-2018 growing seasons at Zillah, Wash. It should be understood that the characteristics described will vary somewhat depending upon cultural practices and climatic conditions, and can vary with location and season. Quantified measurements are expressed as an average of measurements taken from a number of individual trees of the new variety. The measurements of any individual tree or any group of trees, of the new variety may vary from the stated average. All color references herein are based on The 2001 Royal Horticultural Society Colour Chart ($4^{th}$ edition).

Tree:

*Size*.—For observed age and rootstock, considered moderate at approximately 12 feet tall and approximately 20 feet in diameter.

*Vigor*.—Considered moderately high.

*Branching habit*.—Upright and spreading.

*Density*.—Considered moderate.

*Form*.—Trained to open vase.

*Hardiness*.—Considered hardy for region.

*Production*.—Considered moderately high in precocity with a yield of 12 tons per acre based on yields of mature mother tree on 'Mazzard' rootstock and a plant spacing of 20 feet×20 feet.

*Bearing*.—Annual.

Trunk (as measured at harvest maturity):

*Size*.—Circumference at 30 cm above ground is 112 cm.

*Texture*.—20% area smooth with the remainder considered as being rough.

*Color*.—Smooth texture color from the grey-green group 197B. Rough texture color from the grey group 201A.

*Lenticels*.—Numerous and prominent with a horizontal orientation. Length ranges from 15.4 mm to 52.7 mm with an average of 27.8 mm. Width ranges from 1.7 mm to 8.6 mm with an average of 4.1 mm. Number of lenticels average 18 per 9 square centimeters. Color is from grey group 201A.

Branches (as measured at harvest maturity):

*Scaffold branches*.—Texture — Mostly smooth. Size — Circumference at 10 cm from trunk union ranges from 41.0 mm to 46.4 mm with an average of 41.1 mm. Angles as trained range from 60 degrees to 75 degrees from horizontal. Color — From the greyed-purple group N186C. Lenticels — Numerous averaging 14 per 9 square cm. Length ranges from 16.4 mm to 33.6 mm with an average of 24.3 mm. Width ranges from 3.6 mm to 8.8 mm with an average of 6.7 mm. Center color is from the greyed-purple group N186C, outer margin color from the white group N155A.

*Second year fruiting branches*.—Texture — Smooth. Diameter — Ranges from 5.6 mm to 8.8 mm at mid-point of growth with an average of 7.3 mm. Color — From the grey-brown group 199A. Lenticels — Moderate in number averaging 8 per running cm; are round in shape and range from 0.8 mm to 1.4 mm in diameter. Color from the grey-brown group 199C.

*Current year branches*.—Texture — Smooth. Size — Length ranges from 24.5 cm to 45 cm with an average of 34.6 cm. Diameter ranges from 3.6 mm to 5.2 mm, with an average of 4.5 mm at half-way point. Color — Upper surface color from the grey-brown group 199A, lower surface color from the yellow-green group 145A. Internode length — Ranges from 3.0 cm to 5.2 cm with an average of 4.5 cm. Lenticels — moderate in number averaging 5 per running cm; small, round and ranging 1.2 mm to 1.4 mm in diameter; color is from the greyed-orange group 164D.

Flower buds (as measured at full bud swell):

*Spur length*.—Ranges from 15.6 mm to 39.7 mm, with an average of 27.0 mm.

*Bud shape*.—Chordate.

*Number buds per fruiting spur*.—Ranges from 6 to 9 with an average of 8.

*Bud length*.—Ranges from 7.6 mm to 10.0 mm with an average of 8.8 mm.

*Bud diameter*.—Ranges from 4.0 mm to 5.8 mm with an average of 4.8 mm.

*Scale color*.—From the greyed-orange group 174A.

Leaves (with measurements from midpoint of actively growing current season's growth at harvest maturity):

*Blade*.—Size — length ranges from 15.0 cm to 16.5 cm and averages 15.6 cm; width ranges from 5.7 cm to 7.6 cm with an average of 6.3 cm; and thickness averages 0.15 mm. Texture — Upper surface is smooth and leathery, lower surface is smooth with vein protruding above surface. Tip — Acuminate. Base — Oblique. Form/shape — deltoid with acuminate tip. Margin — Serrate. Blade color — Upper surface from the yellow-green group 147A; and lower surface color from the yellow-green group 147B.

*Mid-vein*.—Considered medium large and prominent averaging 1.2 mm in diameter at mid-point of blade with a range of 1.0 to 1.4 mm; and color from the yellow-green group 145D.

*Petiole*.—Averages 4.0 cm in length with a range of 3.5 cm to 4.9 cm; diameter at mid-point ranges from 1.6 mm to 2.2 mm with an average of 1.9 mm; upper surface color is from the greyed-purple group 183A; lower surface color is from the yellow-green group 145D; and a 0.1 mm to 0.3 mm depth groove runs the full length of upper surface.

*Glands*.—Present, kidney shaped and averaging 2.7 mm in length by 1.6 mm in width; with 1 to 3 glands per petiole, mostly 2 alternating in position along grove of petiole and located from 1.0 mm to 8.0 mm from blade base; and color from the greyed-orange group 166B.

*Stipules*.—Not present.

*Attitude*.—Somewhat drooping.

Flowers: Bloom stands out, does not droop.

*Observed first bloom*.—Mar. 27, 2016; Apr. 8, 2017; and Mar. 31, 2018.

*Observed full bloom*.—Apr. 3, 2016; Apr. 16, 2017; and Apr. 8, 2018.

*Size*.—Bloom diameter when fully open averages 33.5 mm and is considered open.

*Bloom count*.—Ranges from 2 to 3 blossoms per bud, mostly 3.

*Petals*.—Five in number; color is from the white group 155C; average length is 17.0 mm; average width is 15.6 mm; and when fully open, petals are considered free.

*Petal shape*.—Round, base is obtuse and the apex is emarginate.

*Nectary color*.—Color is from the yellow-green group 154B.

*Stamens*.—Filament — Average number per bloom is 35; and color is from the white group 155C; and average length is 9.7 mm. Anther — Round in shape, with average 0.45 mm diameter. Pollen — Abundant; and color is from the greyed-orange 163A.

*Carpel*.—Style — Average length is 13.8 mm; and color is from the yellow-green group 149D. Stigma — Clubbed and considered round in shape; with diameter range from 0.5 mm to 0.6 mm; and color from the yellow-green group 151A.

*Sepals*.—Five in number; deltoid in shape, and laid back over thalmus; average base width is 4.8 mm; average length is 6.3 mm; and color is from the yellow-green group 147C, with outside tip highlights from the greyed-red group 181C.

*Peduncle*.—Average length is 26.1 mm; average diameter at mid-length is 0.8 mm; and color is from the green group 137D.

*Thalmus*.—Average depth is 7.0 mm, and average width at the opening is 3.6 mm; urn shaped; and color from the yellow-green group N144B.

Fruit:

*Maturity*.—Harvest maturity Jun. 4, 2018.

*Size*.—Considered large, with average apical diameter 26.3 mm, and average axial diameter is 28.6 mm.

*Form*.—Considered round oblong, with uniform sides.

*Suture*.—Mostly indistinct and narrow, 0.1 mm in width on back side only, generally pushed out from sides giving ribbed appearance, 0.4 mm to 0.5 mm in height.

*Base*.—Uniform cordate in shape; width averages 12.7 mm; and depth averages 4.8 mm.

*Apex*.—Rounded ending in slight distinct depression of 1.0 to 1.5 mm marked by a russetted dot 0.5 mm to 1.0 mm in diameter.

*Peduncle*.—Length ranges from 31.7 mm to 45.9 mm with an average length of 40.2 mm; diameter at mid-point averages 1.1 mm; and color is from the yellow-green group 144A. Skin: Thickness — Considered thin, 0.05 to 0.1 mm. Texture — Surface is smooth and clear, melting in mouth. Tenacity — Considered moderate, and can be peeled without tearing flesh. Tendency to crack — Very light, following rain events. Down — Wanting. Color — Uniform, from the greyed-purple group 187A. Flesh: Color — From the greyed-purple group 184A. Surface of pit cavity color — From the greyed-purple group N186A. Texture — Firm and snappy. Fibers — Considered lightly fibrous. Pit tenacity — Slight around suture line and sides. Ripens — Evenly. Flavor — Sweet and sub acid. Aroma — Slight cherry like. Eating quality — Excellent. Stone: Type — Light-cling type. Size — Considered medium; averages 10.7 mm base to apex, 8.1 mm wide shoulder to shoulder; and 7.5 mm wide suture to suture. Form — Narrow elliptic. Base — Rounded. Apex — Rounded. Sides — Equal. Surface — Smooth. Ventral Edge — Suture is slightly raised 1 mm and is subtended by two low ridges converging basally and apically that averages 3.6 mm wide and 1.2 mm in height at the mid-point, and these ridges are again subtended by two partial ridges extending from base to ⅔ distance to apex and averages 5.6 mm wide at widest point and averages 0.9 mm in height. Dorsal Edge — distinct, smooth, slightly raised ridge from base to apex averages 0.6 mm high and 0.2 mm wide. Color — From the greyed-yellow group — 161D. Tendency to split — None observed. Kernel: Shape — Considered obtus. Base — Rounded. Apex — Acute. Size — Length ranges from 6.8 mm to 7.5 mm with an average of 7.2 mm; width ranges from 4.3 mm to 4.8 mm, with an average of 4.5 mm; and thickness ranges from 2.1 mm to 3.2 mm with an average of 2.9 mm. Color — From the greyed-orange group 164B. Taste — Biter, almond like. Viability — 100% kernel development observed, and viable kernel germination unknown.

*Genetics*.—'TF 7142' has the S1 S4 alleles, while 'Chelan' has an S-allele genotype of $S^3$ $S^9$.

*Pollination requirement*.—'TF 7142' is not self-fertile and in contrast, any cherry cultivar that is self-fertile or does not have an S-allele genotype of $S^1$ $S^4$ would be able to pollinate

*Use*.—Early season, premium fresh market.

*Resistance to insects and diseases*.—Shows no unusual susceptibility nor resistance to any diseases and/or plant or fruit pests of sweet cherry found in the south central region of Washington State.

*Variance in botanical details*.—'TF 7142' exhibits the above described characteristics as grown in Yakima County, in the south central region of Washington state. It is expected that differences may occur when grown in areas exhibiting different growing conditions.

What is claimed:

1. A new and distinct variety of Cherry Tree as illustrated and described herein.

* * * * *